United States Patent [19]

Horrobin et al.

[11] Patent Number: 4,855,136

[45] Date of Patent: Aug. 8, 1989

[54] THERAPEUTIC COMPOSITION AND METHOD

[76] Inventors: David F. Horrobin, c/o Efamol Limited, Egamol House, Woodbridge Meadows, Guildford, Surrey, England, GU1 1BA; Y. Sheng Huang, c/o Efamol Research Inc., Annapolis Valley Industrial Park, P.O. Box 818, Kentville, Nova Scotia, Canada, B4N 4H8

[21] Appl. No.: 92,191

[22] Filed: Sep. 2, 1987

[30] Foreign Application Priority Data

Sep. 10, 1986 [GB] United Kingdom ............... 8621816

[51] Int. Cl.$^4$ ...................... A61K 33/06; A61K 37/02
[52] U.S. Cl. .................................. 424/602; 514/560; 424/678; 424/687
[58] Field of Search ............ 424/128, 153, 156, 195.1, 424/154; 514/557, 560, 899, 192, 251, 906, 929, 899

[56] References Cited

U.S. PATENT DOCUMENTS

| 3,075,880 | 1/1963 | Roth | 424/128 |
|---|---|---|---|
| 4,407,821 | 10/1983 | Mendy | 514/251 |
| 4,415,554 | 11/1983 | Horrobin | 514/560 |
| 4,421,743 | 12/1983 | Alvarez | 424/154 |
| 4,535,093 | 8/1985 | Horrobin | 514/560 |
| 4,695,590 | 9/1987 | Lippman | 514/724 |
| 4,703,060 | 10/1987 | Traitler et al. | 514/549 |

FOREIGN PATENT DOCUMENTS 2118567  4/1983  United Kingdom .

OTHER PUBLICATIONS

Goodman & Gilman's, The Pharmacological Basis of Therapeutics, Gilman et al., 6th Edition, pp. 1460 and 1528, 1985.
"Evening Primrose Oil", Keats Publishing, Inc. ©, 1981, Dr. Richard A. Passwater, pp. 7–9.
"The Nutrition Desk Reference", Keats Publishing Inc. ©, 1985, Garrison et al., pp. 105–106, 58–60.

Primary Examiner—Douglas W. Robinson
Assistant Examiner—Raymond J. Henley, III
Attorney, Agent, or Firm—Nixon & Vanderhye

[57] ABSTRACT

Combinations of gamma-linolenic acid (GLA) and calcium, presented for administration in assimilable dosage unit form in doses of 1 mg to 100 g GLA and 1 mg to 20 g calcium daily, for example, for the treatment of osteoporosis and other bone disorders involving calcium loss from the bones, of premenstrual syndrome, or of hypertension.

3 Claims, No Drawings

THERAPEUTIC COMPOSITION AND METHOD

FIELD OF THE INVENTION

The invention relates to compositions of gamma-linolenic acid (GLA) for use in therapy.

BACKGROUND

Much interest has been shown in essential fatty acids (EFAs) and particularly GLA in recent years, both in relation to prostaglandin (PG) metabolism and generally. The two common series of EFAs are the n-6 series, metabolites of linoleic acid, and the n-3 series, metabolites of alpha-linolenic acid. The structures and naming of the acids may for example be found in the applicants' published European patent specification No. A0132089 (84304610.3) along with a discussion of the role of GLA as a precursor of 1-series PGs and arachidonic acid as precursor of 2-series PGs. This discussion is brief but is given at length in earlier applications also referred to and reference may be made to European patent specification No. A0132089 and the earlier specifications for the whole background.

CURRENT DISCOVERY

In new work, the applicants have found an unexpected and interesting relation between calcium intake and bodily levels of dihomo-gamma-linolenic acid (DGLA) that is the immediate product of GLA in the body and the actual precursor of 1-series PGs. Specifically, the conversion of GLA to DGLA appears to be inhibited by low calcium levels, a conversion previously believed to be readily achieved in the body in all circumstances, such that giving GLA was essentially equivalent to giving DGLA.

In experimental investigations, 16 male Sprague-Dawley rats were maintained for 3 weeks on a diet free of calcium or on an identical diet supplemented with 12.5 g/kg of calcium carbonate. At the end of the period the animals were killed and plasma calcium and fatty acids in various plasma and liver lipid fractions were measured. Mean plasma calcium in the calcium-supplemented group was 2.3 millimolar, whereas it was 1.5 millimolar in the calcium-deficient group. In various lipid fractions there was seen to be accumulation of GLA and its precursor linoleic acid, with depletion of DGLA and its further metabolites. This was most clearly seen in the plasma cholesteryl esters. The fatty acids were extracted from the plasma and separated into various fractions, including cholesteryl esters by thin layer chromatography. The cholesteryl ester fraction was then methylated and subjected to gas liquid chromatography and its fatty acid composition determined. The table below shows the levels of linoleic acid, GLA and DGLA in the plasma cholesteryl esters expressed as mg/100 mg total lipid present. It can be clearly seen that linoleic acid and GLA have accumulated in the calcium deficient animals, while DGLA levels have been sharply reduced

|  | Calcium deficient | Normal calcium |
|---|---|---|
| Linoleic acid | 21.5 ± 4.8 | 16.1 ± 1.6 |
| GLA | 1.7 ± 0.6 | 0.8 ± 0.4 |
| DGLA | 0.6 ± 0.4 | 3.3 ± 1.1 |

DISCUSSION

This fivefold reduction in DGLA levels in the deficient animals has suggested to the Applicants that where low levels of calcium are present it is important to ensure that GLA cannot itself be a limiting factor. In conditions such as Paget's disease and osteoporosis and other bone disorders involving calcium loss from the bones, calcium may be given, indeed it has been reported to be of benefit in the treatment of osteoporosis, but it cannot be certain that it is functionally effective. Given the importance of essential fatty acid conversion in the n-6 series, especially in the effects on PG balance discussed for example in the applicants' earlier patents, and given that by-passing the newly discovered poor conversion of GLA to DGLA by administering DGLA is impractical as there are no significant natural sources of DGLA, administration of GLA with the calcium is important to ensure that DGLA production is as great as possible. Maximum use of the available capacity is made through ample GLA levels.

Further, the role of calcium in GLA conversion suggests calcium supplementation in conditions where giving GLA has been proposed as in itself of value. Such conditions are the subject of numerous prior patent applications by the applicants but attention is particularly directed to value in the treatment of premenstrual syndrome and of hypertension. Both these conditions have been the subject of previously little remarked reports that calcium is of benefit in their treatment. In the light of their new work the applicants see these reports as of considerable significance and as suggesting an improvement in their own proposed treatment of these conditions with GLA, consisting in the use of calcium at the same time.

STATEMENT OF INVENTION

The invention thus lies in

1. Therapeutic combinations of GLA and calcium in which GLA in an assimilable form is presented for administration in doses ranging from 1 mg to 100 g per day, preferably 150 mg to 3 g per day, in combination with calcium in an assimilable form in doses ranging from 1 mg to 20 g per day, preferably 500 mg to 3 g per day. Appropriate sources of calcium include, but are not limited, to calcium chloride, calcium gluconate, calcium lactate, calcium carbonate, calcium phosphate, calcium levulinate and calcium glubionate. Routes of administration include, but are not limited to, oral, parenteral and topical.

2. Methods of treating osteoporosis and other bone disorders involving calcium loss from the bones, or hypertension, or premenstrual syndrome by administering GLA (as above) in combination with calcium (as above).

The invention also extends to the use of said GLA and calcium together or separately for the manufacture of a medicament for use in the treatment of the said conditions.

FORMS AND SOURCES OF GLA

The GLA can be and indeed normally will be used as a pharmaceutically acceptable and physiologically equivalent derivative and reference to GLA is to be taken as including reference to such derivatives. Identification of useful derivative is by their having the valuable effect in the body of the acid itself, but conversion can be shown directly by gas chromatographic analysis of concentrations in blood, body fat, or other tissue by standard techniques, for example those of Pelick et al., p.23, "Analysis of Lipids and Lipoproteins" Ed. Perkins, American Oil Chemists Society, Champaign, Ill., U.S.A.

Convenient derivatives of GLA include salts, amides, esters including glyceride esters and alkyl (e.g. $C_1$ to $C_4$) esters, and phospholipids.

If desired, pharmaceutical compositions may be produced for use in the invention by associating the natural or synthetic acid, as such or as a derivative, with an acceptable pharmaceutical vehicle. It is, however, at present convenient to incorporate at least the gamma-linolenic acid into compositions in the form of an available oil having a high gamma-linolenic acid content, hence references to "oil" herein.

At the present time known natural sources of oils having a high GLA acid content are few (there are no known natural sources of significant amounts of dihomo-gamma-linolenic acid). One source of oils currently available is the seed of evening primrose species such as *Oenothera biennis L.* and *Oenothera lamarckiana*, the oil extract therefrom containing GLA (about 8%) and linoleic acid (about 72%) in the form of their glycerides together with other glycerides (percentages based on total fatty acids). Other sources of GLA are Borage species such as *Borago officinalis* which, though current yield per acre is low, provide a richer source of gamma-linolenic acid than Oenothera oil. Recent studies on fungi which can be cultivated by fermentation promise a fungal oil source.

The oil is extracted from the seed by one of the conventional methods of extraction such as cold pressure, screw pressure after partially cooking the seed or solvent extraction.

Fractionation of a typical sample of this oil in the form of methyl esters shows the relative proportions:

| Palmitate | 6.15 |
| Stearate | 1.6 |
| Oleate | 10.15 |
| Linoleate | 72.6 |
| Gamma-Linolenate | 8.9 |

As a preservative, alpha-tocopherol is added to the oil in a concentration 0.1%.

The seed oil extracts referred to above can be used as such or can, for example, if desired, be fractionated to yield an oily composition containing the triglycerides of gamma-linolenic and linoleic as the main fatty acid components, the gamma-linolenic acid content being if desired a major proportion. Seed oil extracts appear to have a stabilising effect upon dihomo-gamma-linolenic acid if present.

VETERINARY APPLICATIONS

It will be understood that where a disorder of a kind calling for treatment in animals arises, the invention while described primarily in terms of human medicine and treatment is equally applicable in the veterinary field.

PACKS

If it is not desired to have compositions comprising different active materials together, packs may be prepared comprising the materials presented for separate, or part joint and part separate administration in the appropriate relative amounts, and use of such packs is within the purview of this invention.

DIETARY COMPOSITIONS

The invention is chiefly described in terms of methods of treatment and pharmaceutical compositions, but it will be understood that the gamma-linolenic and other acids, being in the nature of dietary supplements, could be incorporated in a dietary margarine or other foodstuffs for use by those taking calcium.

PHARMACEUTICAL PRESENTATION

The compositions according to the invention are conveniently in a form suitable for oral, parenteral, etc. administration in a suitable pharmaceutical vehicle, as discussed in detail for example in Williams British patent specification No. 1,082,624, to which reference may be made, and in any case very well known generally for any particular kind of preparation. Thus, for example, tablets, capsules, ingestible liquid or powder preparations can be prepared as required. Injectable solutions of hydrolysed Oenothera oil may be prepared using albumin to solubilise the free acid.

It will be understood that the absolute quantity of active materials present in any dosage unit should not exceed that appropriate to the rate and manner of administration to be employed but on the other hand should also desirably be adequate to allow the desired rate of administration to be achieved by a small number of doses. The rate of administration will moreover depend on the precise pharmacological action desired.

EXAMPLES

The following are specific examples of the invention, against the conditions set out:

Example 1

A capsule containing 60% evening primrose oil 0.5 g administered six times per day with calcium gluconate tablets 0.5 g.

Example 2

A 0.25 g capsule containing 150 mg of GLA administered 3 times per day with calcium carbonate tablets 1 g.

A pack as referred to herein comprises 500 mg capsules of eveining primrose oil as above, to be taken 6 per day, together with calcium carbonate tablets.

Preparations of compositions as referred to herein is exemplified for example by the preparation of 0.5 g capsules of evening primrose oil as above and for example calcium carbonate tablets as above, or, for example by combining in tablet form calcium gluconate 0.5 g per tablet and GLA 150 mg per tablet.

We claim:

1. A method of treating bone disorders involving calcium loss from the bones in a person in need thereof comprising administering to the person the combination, in dosage unit form, of gamma-linolenic acid in an assimilable form and in an amount of from 1 mg to 100 g per day together with calcium in an assimilable form and in an amount of from 1 mg to 20 g per day.

2. The method of claim 1, in which the daily dosage of gamma-linolenic acid is from 150 mg to 3 g and the daily dosage of calcium of from 500 mg to 3 g.

3. The method of claim 1, in which the bone disorder is osteoporosis.

* * * * *